United States Patent [19]

Libit

[11] 4,005,109

[45] Jan. 25, 1977

[54] PREPARATION OF PROSTAGLANDIN INTERMEDIATES

[76] Inventor: Lawrence Libit, 639 Library Place, Evanston, Ill. 60201

[22] Filed: June 24, 1974

[21] Appl. No.: 482,083

[52] U.S. Cl. .................. 260/343.3 R; 260/345.8; 260/345.9; 260/468 D; 260/514 D

[51] Int. Cl.² .................................. C07D 307/83

[58] Field of Search ............ 260/343.3, 483, 345.8

[56] References Cited

UNITED STATES PATENTS

| | | | |
|---|---|---|---|
| 2,268,169 | 12/1941 | Sauer | 260/483 |
| 3,711,515 | 1/1973 | Kelly | 260/343.3 |
| 3,778,461 | 12/1973 | Brown et al. | 260/343.3 |
| 3,781,306 | 12/1973 | Kelly | 260/343.3 |
| 3,816,460 | 6/1974 | Kelly | 260/343.3 |
| 3,816,461 | 6/1974 | Kelly | 260/343.3 |
| 3,816,462 | 6/1974 | Kelly | 260/343.3 |
| 3,818,045 | 6/1974 | Kelly | 260/343.3 |
| 3,823,138 | 7/1974 | Rheenen | 260/343.3 |

OTHER PUBLICATIONS

Wagner et al., Syn. Org. Chem. p. 407 (1955).
J. Am. Chem. Soc. vol. 94 pp. 4014–4015 (1972).

*Primary Examiner*—Lewis Gotts
*Assistant Examiner*—D. R. Phillips
*Attorney, Agent, or Firm*—Wallenstein, Spangenberg, Hattis & Strampel

[57] ABSTRACT

Preparation of prostaglandin intermediates by reacting mon-tetrahydropyranyl ether, in a diethyl ether medium containing pyridine, with malonyl dichloride, reacting the resulting malonic acid chloride with triethylamine in a diethyl ether medium to produce a ketone derivative, followed by heating to effect ring closure, then reduction, then cleaving the cyclobutyl ring followed by epimerization to produce the "Corey" intermediate. Those intermediates which are novel are also claimed.

6 Claims, No Drawings

PREPARATION OF PROSTAGLANDIN INTERMEDIATES

My invention is directed to the preparation of certain intermediates which have particular use in processes for producing prostaglandins. More specifically, it is directed to a process for producing the so-called Corey intermediate which, as is well known, may be illustrated by the following formula

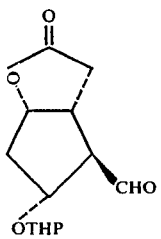

E. J. Corey et al., *J. Am. Chem. Soc.*, 93, 1490 (1971); E. J. Corey, *Ann. N. Y. Acad. Sci.*, 180, 24 (1970).

Routes to the preparation of prostaglandins starting with the Corey intermediate are well known to the art and such routes possess a number of significant advantages over various other known procedures for the preparation of prostaglandins. However, process routes heretofore known for the preparation of the Corey intermediate, starting with readily available materials, are cumbersome and time-consuming and involve a very substantial number of steps with the result that the preparation of the Corey intermediate is very costly. Furthermore, the Corey intermediate is a rather unstable product and, since it cannot satisfactorily be kept for any substantial or appreciable period of time without breakdown or destruction, it is necessary to use it within a relatively short period of time after it has been prepared for the further processing thereof in the preparation of prostaglandins therefrom.

In accordance with my invention, the Corey intermediate is prepared in good yields by a process which involves only a very few steps from the starting material referred to below. Furthermore, the process can be stopped just short of the preparation of the Corey intermediate with the production of a novel product, which is an intermediate for the Corey intermediate, which aforesaid novel product has good stability over a relatively substantial period of time. The result is that said stable product can be prepared and stored or shipped as such and then readily and easily converted to the Corey intermediate at such time as it is desired to carry out the production of prostaglandins from the Corey intermediate.

My invention may be illustrated by the following reaction scheme:

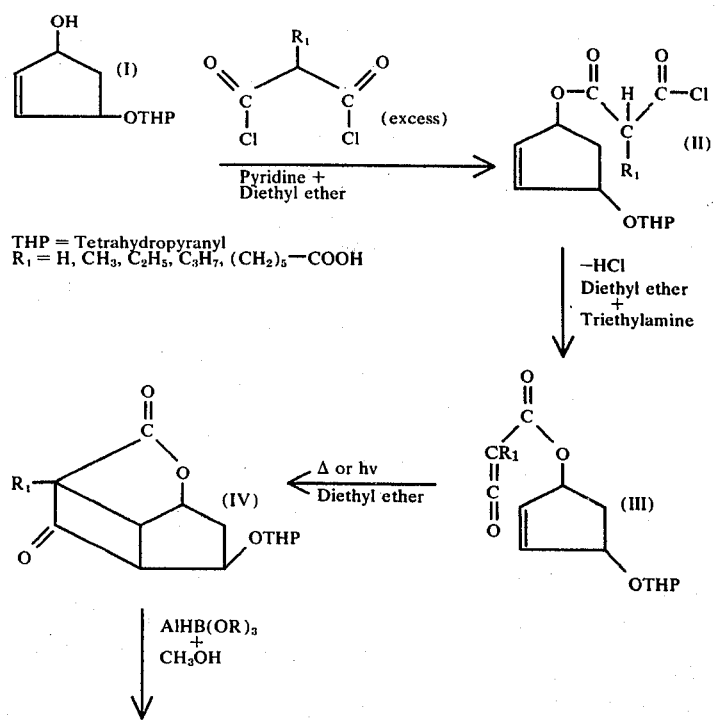

-continued

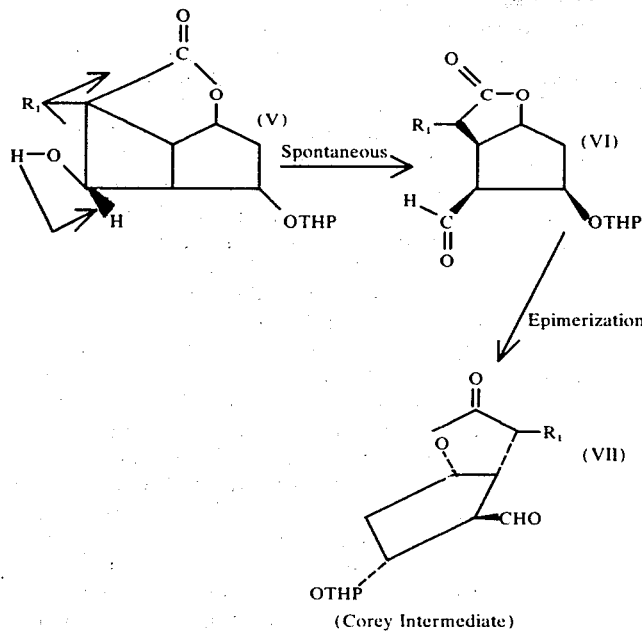

(Corey Intermediate)

Stated briefly, and as may be noted from the above, the Corey intermediate, starting with mono-tetrahydropyranyl ether, is produced by a series of steps which comprise (1) ketene addition, (2) selective reduction of the resulting cyclobutanone derivative, and (3) cyclobutyl cleavage followed by treatment with a weak proton source (e.g. 1 equivalent of methanol) whereby to produce the Corey intermediate. The several reactions, generally speaking, can be carried out in a single reactor. The starting mono-tetrahydropyranyl ether is readily produced from commercially available cyclopentene-1,4-diol, utilizing the procedure described by E. J. Corey et al., *J. Am. Chem. Soc.*, 94, 4014 (1972).

In more specific terms, an organic solvent solution, particularly a diethyl ether solution, of mono-tetrahydropyranyl ether, is reacted with malonyl dichloride, or an alkyl or substituted alkyl derivative thereof (hereafter called "malonyl dichloride product"), in the presence of pyridine at a low temperature, for instance, initially at about 0°–5° C. for a number of hours and the reaction mixture is then permitted to rise to about room temperature and the excess malonyl dichloride is then removed, conveniently by pumping it off at high vacuum (for instance, 2 mm of mercury) at 25°–60° C. The resulting malonic acid chloride of the monotetrahydropyranyl ether is then converted to a ketene intermediate by reacting it in a dry ether solution with triethylamine at low temperature, for instance, about 0°–5° C. The ketene intermediate is then heated, under refluxing conditions, at a temperature for instance of the order of 40°–60° C which results in ring closure, namely, to produce a cyclobutanone derivative. The latter compound is then reduced to the corresponding alkoxide of the alcohol. Such reduction can be effected by various reducing agents, which should not be used in excess amounts, such as, by way of example, sodium borohydride/tetrahydrofuran (NaBH$_4$/THF), or triisobutoxy aluminum hydride [AlH(OR$_3$)] where R is isobutoxy. Then, on addition of methanol, ring opening is effected to produce the essentially all cis-isomer of the Corey intermediate. Finally, upon addition of methanol containing a trace amount of sodium carbonate, epimerization takes place whereby to produce the Corey intermediate.

The following non-limiting Example is illustrative of the process of my invention.

EXAMPLE a. Preparation of Intermediate Compound (I) and Derivatives Thereof

1. A solution made up of 10 mmoles of the mono-tetrahydropyranyl ether (Compound I), 100 ml of dry diethyl ether and 10 mmoles of pyridine is added to 20 mmoles of malonyl dichloride at 0° to 5° C. At the end of 20 hrs. the reaction mixture is allowed to rise to room temperature and is maintained at room temperature for about 1 hr. The excess malonyl dichloride is then pumped off at high vacuum to leave as a residue Compound (II). The infrared (IR) and nuclear magnetic resonance (NMR) spectra of said Compound (II) are consistent with the indicated structure.

2. The procedure of part (1) of this Example is carried out and the Compound (II) residue is triturated with dry diethylether which results in the production of an approximately 90% yield of Compound (II).

3. To the aforesaid Compound (II) produced in part (1) or part (2) of this Example, an excess of methanol is added whereby the methyl ester of Compound (II) is formed in a yield ranging generally from about 50 to about 90%. The IR, NMR and elemental analyses of said methyl ester of Compound (II) are also consistent with said indicated structure.

b. Conversion of Intermediate Compound (II) to Intermediate Compound (III)

To a solution made up of 10 mmoles of Intermediate Compound (II), prepared as described in part (1) or part (2) of part (a) of this Example, in 100 ml of dry diethylether, there are added 100 mmoles of triethylamine at 0° to 5° C. The resulting solution is allowed to warm to room temperature and then 10 ml of deuterated methanol are added. The resulting methyl ester of Intermediate Compound (II) is isolated. Analysis by NMR shows a loss of one proton which indicates that the central carbon in the β-diester linkage is mono deuterated, and the mass spectral fragmentation pattern confirms the presence of one deuterium. The NMR splitting pattern of the central CH$_2$ grouping in the β-diester of Intermediate Compound (II) when compared to the deuterated diester also indicates one deuterium has been incorporated. The foregoing indicates that the intermediate ketene (Compound (III)) is formed. On repeating the procedure, said ketene is allowed to warm to room temperature and then refluxed for 3 hrs. at 40°–60° C. At this time, a new product is observed by TLC (thin layer chromatography), and a quick chromatography on silica gel gives an approximately 60% overall yield (based on Compound (II)) of Compound (IV), identified by IR, NMR, mass spectral and elemental analyses.

c. Conversion of Intermediate Compound (IV) to Intermediate Compound (VI)

To 10 mmoles of Compound IV, in the form of a solution in 100 ml of dry tetrahydrofuran or benzene, there are added, dropwise, 10 mmoles of tri-isobutoxy aluminum hydride, or other reducing agents, to effect reduction to the corresponding aluminum alkoxide. The use of appreciable excess of reducing agent or protonic solvents should be avoided. Then, on addition of 10 ml of methanol, ring opening is effected to produce essentially the all cis-isomer of the Corey intermediate in an approximately 60 to 90% yield. So far as I am aware, the all cis-isomer has never been definitely identified in the literature.

d. Conversion of Intermediate Compound (VI) to Corey Intermediate

Ten mmoles of Compound (VI) are admixed with 10 ml of methanol containing a trace of sodium carbonate and allowed to stand at room temperature for 10 minutes to effect epimerization whereby to produce Compound (VII), the heretofore known Corey intermediate. Compound (VII) is identified as the Corey Intermediate by comparison with an authentic sample of the latter, using IR, NMR and mass spectral analyses. The said Compound (VII) is rather unstable. It is convertible into various prostenoids in high yields by procedures known to the art.

I claim:

1. In a process for producing intermediates useful in the production of prostaglandins, the steps which comprise:

a. providing a solution of monotetrahydropyranyl ether in diethyl ether and pyridine, said mono-tetrahydropyranyl ether having the formula

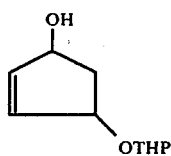

where THP is tetrahydropyranyl, b. admixing said solution with a malonyl dichloride product in proportions to produce a malonic acid mono-ester chloride of mono-tetrahydropyranyl ether, and c. then reacting the same with triethylamine in a diethyl ether medium to produce a compound having the formula

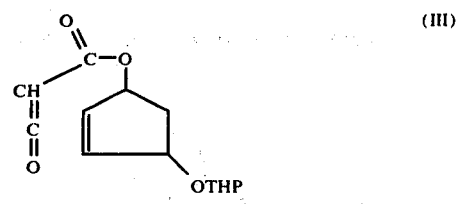

d. heating the Compound (III) in a diethyl ether medium to produce a compound having the formula

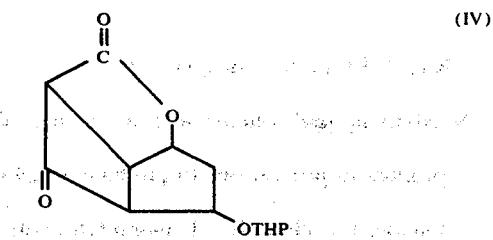

e. reducing Compound (IV) with a reducing agent in the presence of methanol to produce a compound having the formula

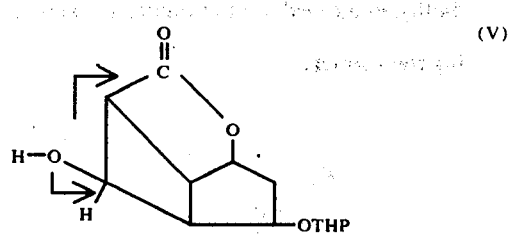

f. effecting cyclobutyl cleavage of Compound (V) to produce a compound having the formula

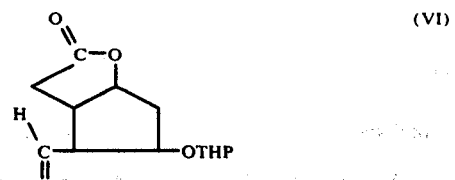

g. and epimerizing Compound (VI) to produce the compound having the formula

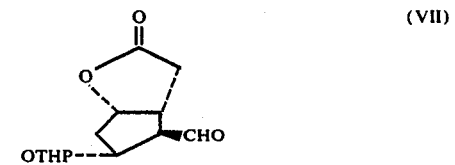

2. In a process for producing intermediates useful in the production of prostaglandins, the steps which comprise:

a. providing a solution of monotetrahydropyranyl ether in diethyl ether and pyridine, said mono-tetrahydropyranyl ether having the formula

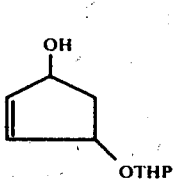

where THP is tetrahydropyranyl.

b. admixing said solution with a malonyl dichloride product in proportions to produce a malonic acid mono-ester chloride of mono-tetrahydropyranyl ether, and c. then reacting the same with triethylamine in a diethyl ether medium to produce a compound having the formula

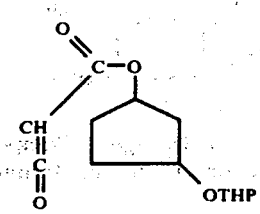

(III)

and then d. heating the Compound (III) in a diethyl ether medium to produce a compound having the formula

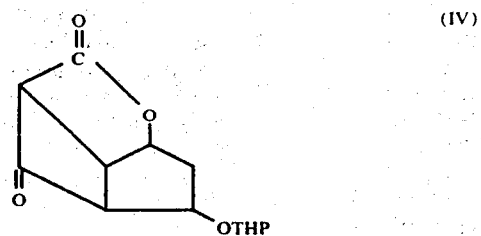

(IV)

3. The process of claim 2, wherein the malonyl dichloride product is malonyl dichloride.

4. The process of producing a compound having the formula

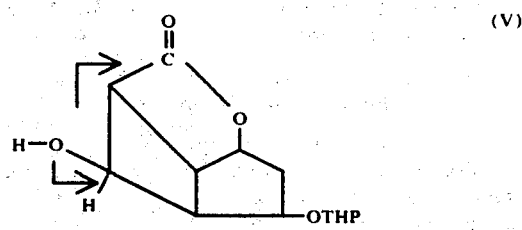

(V)

which comprises reducing the compound (IV) of claim 2 with a reducing agent in the presence of methanol.

5. The process of producing a compound having the formula

(VI)

which comprises effecting cyclobutyl cleavage of the compound of (V) of claim 4.

6. The process of producing the compound having the formula

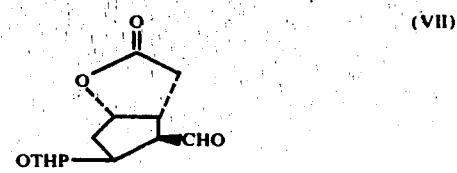

(VII)

which comprises epimerizing the compound (VI) of claim 5.

* * * * *